United States Patent
Wadman

(10) Patent No.: US 7,554,665 B2
(45) Date of Patent: Jun. 30, 2009

(54) DUAL BEAM SET-UP FOR PAROUSIAMETER

(75) Inventor: Sipke Wadman, Waalre (NL)

(73) Assignee: Koninklijke Philips Electronics N.V., Eindhoven (NL)

(*) Notice: Subject to any disclaimer, the term of this patent is extended or adjusted under 35 U.S.C. 154(b) by 0 days.

(21) Appl. No.: 12/063,126

(22) PCT Filed: Aug. 4, 2006

(86) PCT No.: PCT/IB2006/052702

§ 371 (c)(1),
(2), (4) Date: Feb. 7, 2008

(87) PCT Pub. No.: WO2007/020554

PCT Pub. Date: Feb. 22, 2007

(65) Prior Publication Data

US 2008/0192258 A1    Aug. 14, 2008

Related U.S. Application Data

(60) Provisional application No. 60/708,321, filed on Aug. 15, 2005.

(51) Int. Cl.
*G01N 21/47* (2006.01)
*G01J 1/04* (2006.01)
(52) U.S. Cl. .................... 356/446; 356/445; 356/236
(58) Field of Classification Search ......... 356/445–448, 356/236, 600, 625, 511
See application file for complete search history.

(56) References Cited

U.S. PATENT DOCUMENTS

| | | | |
|---|---|---|---|
| 2,246,501 A | 6/1941 | Bradner et al. | |
| 4,093,991 A | 6/1978 | Christie, Jr. et al. | |
| 4,575,252 A | * 3/1986 | Akiyama | 356/446 |
| 4,770,536 A | 9/1988 | Golberstein | |
| 5,241,369 A | 8/1993 | McNeil et al. | |
| 5,745,234 A | * 4/1998 | Snail et al. | 356/236 |

(Continued)

FOREIGN PATENT DOCUMENTS

DE    3312948    12/1983

(Continued)

OTHER PUBLICATIONS

Wadman et al., "Appearance Characterisation by a Scatterometer Employing a Hemispherical Screen", Proceedings of SPIE, vol. 5189, Surface Scattering and Diffraction III., pp. 163-173, XP002360323.

*Primary Examiner*—Sang Nguyen

(57) ABSTRACT

A parousiameter having a dual beam setup and method for use thereof is provided for producing measurements of optical parameters. The dual beam parousiameter includes a hemispherical dome enclosure 318 sealed at the bottom with a base 320. A radiation source 302 produces radiation in two beams, an illumination beam 304 for illuminating a sample surface 308 and a calibration beam 330 for providing optical characterization information about the illumination beam 304. Each beam is guided into the hemispherical dome enclosure 318 via separate optical paths. An optical imaging device 324 is positioned to acquire an image of scatter radiation 314 scattered by the sample surface 308 illuminated by the illumination beam 304, and acquire an image of the calibration beam, simultaneously. The calibration beam image is used to compensate for variability in optical output of the radiation source 302 when analyzing the scatter radiation data.

11 Claims, 6 Drawing Sheets

U.S. PATENT DOCUMENTS

| | | | |
|---|---|---|---|
| 5,912,741 A | 6/1999 | Carter et al. | |
| 6,034,776 A * | 3/2000 | Germer et al. | 356/369 |
| 6,577,397 B1 * | 6/2003 | Wadman | 356/446 |
| 6,631,000 B1 | 10/2003 | Schwarz | |
| 7,256,895 B2 * | 8/2007 | Castonguay | 356/511 |
| 7,349,096 B2 * | 3/2008 | Wadman | 356/446 |
| 2004/0207836 A1 | 10/2004 | Chhibber et al. | |

FOREIGN PATENT DOCUMENTS

| | | |
|---|---|---|
| EP | 0967459 | 9/2004 |
| GB | 2227308 | 7/1990 |
| WO | WO0037923 | 6/2000 |
| WO | WO2004076992 | 9/2004 |
| WO | WO2004077032 | 9/2004 |
| WO | WO2004077033 | 9/2004 |

* cited by examiner

DUAL BEAM SET-UP FOR PAROUSIAMETER

CROSS REFERENCE TO RELATED APPLICATIONS

This application claims the benefit of International Application Number PCT/IB2006/052702, filed Aug. 4, 2006, and U.S. Provisional Application Ser. No. 60/708,321 filed Aug. 15, 2005 which are incorporated herein whole by reference.

The present disclosure relates generally to an apparatus for characterizing optical properties of materials. More specifically, the present disclosure provides a dual beam parousiameter for performing optical measurements of materials.

In the current global economy, manufacturing of a product rarely occurs at one manufacturing plant. Components are fabricated at various plants around the world and shipped to a final fabrication site where all the components are incorporated into the final product. This global manufacturing supply chain has a host of benefits, most notably cost reduction, which can be passed on to the consumer. However, drawbacks exist in such a distributed manufacturing process.

One problem encountered, when product components are fabricated in distributed locations, is a consistency in the optical properties of a product housing (e.g., color, gloss, texture, etc.). Corporations spend millions on market research to create products that appeal to the consumer and are easily differentiated from competing products (i.e., brand recognition), whether by having a Nike 'Swoosh' on a shoe or t-shirt, or the distinctive case design of the Apple iMac line of computers. Unfortunately, a brand's appeal can suffer from manufacturing that appears inconsistent.

As an example, consider the manufacture of a television set; the internal circuitry may be fabricated in Taiwan, the CRT in South Korea, the front housing in Malaysia and the rear housing in the Philippines. Often it is quite difficult to manufacture the front and rear housings with the same optical properties, even when the same materials and dyes are used. The equipment calibration errors, mechanical wear, as well as a host of other factors contribute to the inconsistencies. The end result is a television set in which the front housing has a different appearance than the rear housing. Such non-uniformity of color, gloss, texture, etc. are readily noticed by consumer and the impression given is one of low quality.

Many surfaces of industrial products have a physical structure with certain properties as to enhance the functionality of the product or to improve its appearance. A few typical examples are the extremely smooth surfaces of high quality optical components, wear-resistant layers on cutting tools, the surface of paints, the finely textured plastic parts of surfaces of cosmetics packages and decorative personal care products, the pressing of rolling textures produced in sheet metal, and the high gloss metallic-looking lacquers for the automotive industry.

These and many other products are said to have a surface texture. Texture is recognized as the property that determines the human interface, in other words generally how a product feels and looks. The "looks-part" of the texture is called the optical appearance. The optical appearance is a result of what the surface does with light incident on the surface from the environment. Incident light comes from many directions in many cases and it can be reflected, transmitted, re-emitted, absorbed, colored, diffused and scattered by surface roughness or structures or by the presence of small particles.

The assessment of textures for optical appearance is usually made in one or more of three methods: visual comparison, gloss and color measurement, and mechanical surface geometry measurement.

Visual assessments are made by visually comparing a product surface to certain standard textured surfaces by trained personnel. Visual appearance is governed by the geometrical outline of the surface and the optical properties of the material itself. Visual texture assessment of e.g. scratches is very difficult with light-colored surfaces, because there the texture influence is overwhelmed by the strong reflection. White, moderately rough or fine surfaces do not look very different to the eye.

A gloss meter is a simple device that projects a light beam on the surface and measures the intensity ratio of the specular reflected beam and the diffused light in a halo around the specular reflection. This is done under fixed angles of incidence, often 30 or 60 degrees.

Mechanical micro-geometrical measurements with contact probes (surface-tests) generate 1-D, 2-D or 3-D maps of the surface. By mathematical evaluation many statistical variants can be obtained by this method, like the well-known roughness measure $R_a$, average slope or peak counts. The method tries to find a relation between the optical appearance of the surface and its geometry.

The latter two methods attempt to define certain figures of merit, derived statistically from observational data that have a relation to the optical appearance.

In general terms, the limitations of these methods originate from the indirectness of the measured parameters. As an example, condensed statistical data derived from a surface measurement comprises a few merit figures that describe the geometrical shape of the surface texture quite well. The proposition is that there exists a relation between the geometrical data and how the surface looks to the eye. The subjective and personal factor makes this relation erratic and irreproducible.

As a second problem, there is the limitation of incomplete data fields. A gloss meter measures optical properties, but does so in a very limited way: only one incidence angle and two (direct and forward scattered) directions of reflection. This does not address the wealth of variability of surfaces, angles of incidence effects, azimuthal effects, and hemispherically strayed light. The optical appearance of a product is determined by the sum of all reflected light (or re-emitted by translucent materials) in the entire hemisphere, originating from incident light from the entire hemispherical environment.

The optical appearance of a textured surface (all surfaces have a texture, natural or purposely added) is formed by light reflected off this surface and entering the eye. Assuming a parallel light beam illuminating a moderately rough surface such as an automobile dashboard, part of the light reflects specularly in a certain direction, but a part also diffuses in other directions. Such a surface is said to be not perfectly diffuse. As seen in FIG. 1, the eye 1 captures light diffused off the product from different parts 3, 4 of the surface 2 under different angles. This light may have different intensities at different angles, so the surface may appear to have different brightness at different parts of the products, e.g. darker at lower angles.

Any light diffused in other directions than captured by the eye is lost to the eye altogether. The same is true for the usual form of gloss meters. If a light beam is aimed at a surface, it is necessary to measure the light diffused in all directions in the upper hemisphere, not integrated but with directional resolution, to fully describe the optical behavior. To be complete, this should be done for incident light from any direction within the entire hemisphere, i.e. under all vertical (ascension) and horizontal (azimuth) angles. The full image of the directions and intensities of the diffused radiation can be obtained by measuring this hemispherical intensity distribution for multiple combinations of incident height and azimuth. The usual method for such measurements is to scan the entire hemisphere with a scatterometer with a moving detector as known from, inter alia, the German patent application no. 33 12 948. A complete measurement takes many hours in practice.

A parousiameter as disclosed in U.S. Pat. No. 6,577,397, issued to the present inventor on Jun. 10, 2003 and herein incorporated by reference, illuminates a surface in an optically controlled fashion and measures the reflections in a full hemisphere. Brightness changes and various flop effects—color or brightness shifts which occur as a viewer changes viewing angle—are exposed under various illuminations, as well as any other optical anisotropies. Software then converts these measurements into merit factors adapted to specific quality control parameters. Using a parousiameter with pre-taught characterizations, a full measurement can be performed in as little as 15 seconds.

As shown in FIG. 2, in a typical parousiameter is comprised of a dome 10 coated with a diffuse neutral gray coating, and a dull black base plate 11 with a central hole 12 through which a part of a sample surface is visible. A vertical slot 13 formed on the surface of the dome is fitted with a light source 14, which projects a light beam 15 on the sample. The light source can be moved to different heights or inclinations with the beam aiming at the sample all the time. The light source may be arranged away from the dome, the radiation beam being guided to the dome by a fiber-optic cable. Next to the sample an off-axis convex mirror 16 is placed. Right above this mirror there is a imaging device port 17 for a video imaging device to look at the image of the dome surface reflected in the mirror, which is designed to reflect the entire inside of the dome. The illuminated area of the sample can be adjusted by a diaphragm (not shown) in the light path from approximately Ø12 mm to Ø2 mm. The spot is focused on the dome and has a diameter of ≈30 mRad. The resolution can be further improved to 1-5 mRad. The reflective wide-angle system 16 in FIG. 2 forms, in general, a deformed image of the inner dome surface. A regular, array of dark marks may be applied to the dome in order to calibrate the image deformation by the optical system. The dark marks are useful for subsequent software correction of the image and transformation to a real spherical stereographic projection. The dark marks need not be used in all measurements, but are useful for calibration measurements. The correction of the deformation may alternatively be calculated by ray-tracing or mathematically if the shapes of the surfaces are known.

The light source used in a parousiameter, typically a halogen incandescent bulb, experience intensity drifts over time even when supplied by a well stabilized DC voltage source, frequently resulting in variations of a few percent. This instability is a problem for other types of optical measurement equipment, as well. The standard methodology for compensating for the light intensity variations is to bracket a series of sample measurements with a blank measurement before and a second after the sample measurements. These blank measurements are used as calibration measurements to track the intensity variation from the initiation of the sample measurements until the completion of the last sample measurement in the series. However, the elapsed time between the first blank measurement and the second blank measurement may be in excess of an hour.

An object of the present disclosure is to provide lamp measurements simultaneously with the sample measurement in each image, thus each image contains its own calibration reference for the light source output.

The present disclosure accomplishes the above-mentioned objective by providing two radiation beams, an illumination beam and a calibration beam, from a radiation source. The illumination beam is guided towards a sample surface, whereupon the illumination beam illuminates the sample surface. Illumination of the sample surface results in radiation being scattered by the sample surface. This scattered radiation, in turn, impacts a projection screen, which is imaged by an imaging device, e.g., digital camera, digital video camera, etc. A wide angle, fisheye lens, or convex mirror is used to allow the imaging device to image a maximum projection screen surface.

The calibration beam is directed to the imaging device, such that the projection screen image data and the calibration beam data are simultaneously imaged by the imaging device.

The apparatus for characterizing the optical appearance of a sample surface includes a housing formed by a hemispherical dome and a base. The hemispherical dome has a first aperture formed at an apex, a second aperture formed at a position offset from the apex, and a third aperture formed at a bottom position of the hemispherical dome and perpendicular to the apex, and at least a portion of the inside surface of the hemispherical dome is configured as a projection screen.

The base is configured and positioned to support the hemispherical dome, such that the base and dome form an enclosed hemispherical volume. An opening is formed on the base and positioned opposite the first aperture. The sample surface is positioned against the outside surface of the base so that at least a portion of the sample surface is visible through the first aperture and the opening. A secondary mirror is disposed on an inside surface of the base and positioned vertically opposite the second aperture and horizontally opposite the third aperture.

An optical imaging device, aligned with the second aperture and the secondary mirror, and a radiation source are positioned outside the enclosed hemispherical volume.

The radiation source produces a first radiation beam, which is directed along a first optical path originating at the radiation source, passing through the first aperture and the opening and terminating at the sample surface at an incident angle. A second radiation beam emitted by the radiation source simultaneous to emission of the first radiation beam, is directed along a second optical path originating at the radiation source, entering the enclosed hemispherical dome through the third aperture, redirecting through the second aperture and terminating at said optical imaging device.

These and other features, aspects, and advantages of the present invention will become better understood with regard to the following description, appended claims, and accompanying drawings wherein:

Figure 1:
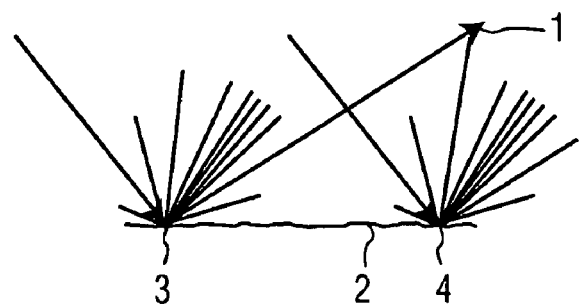
FIG. 1 illustrates a ray representation of incident light scattering from a textured surface.
Figure 2:
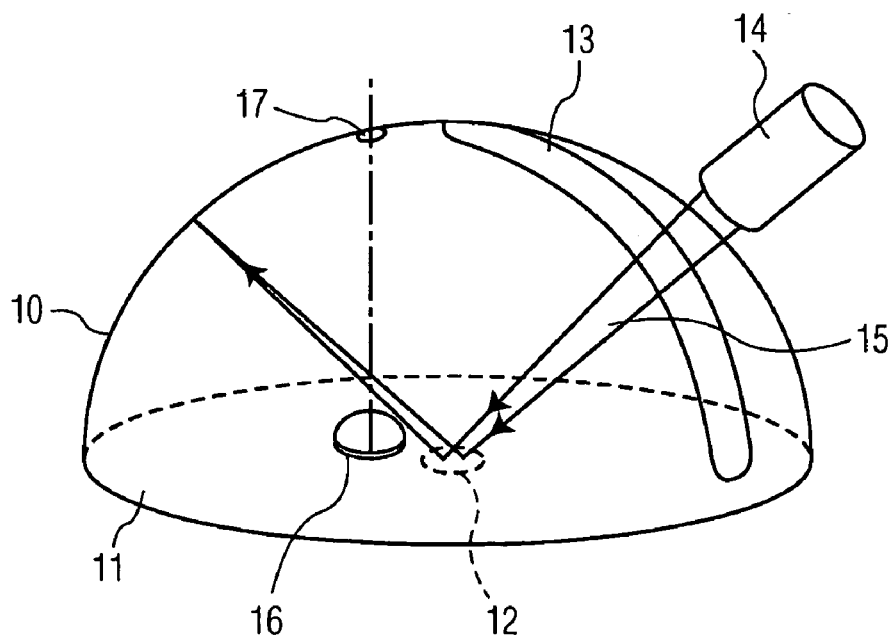
FIG. 2 illustrates an embodiment of a prior art single beam parousiameter.
Figure 3:
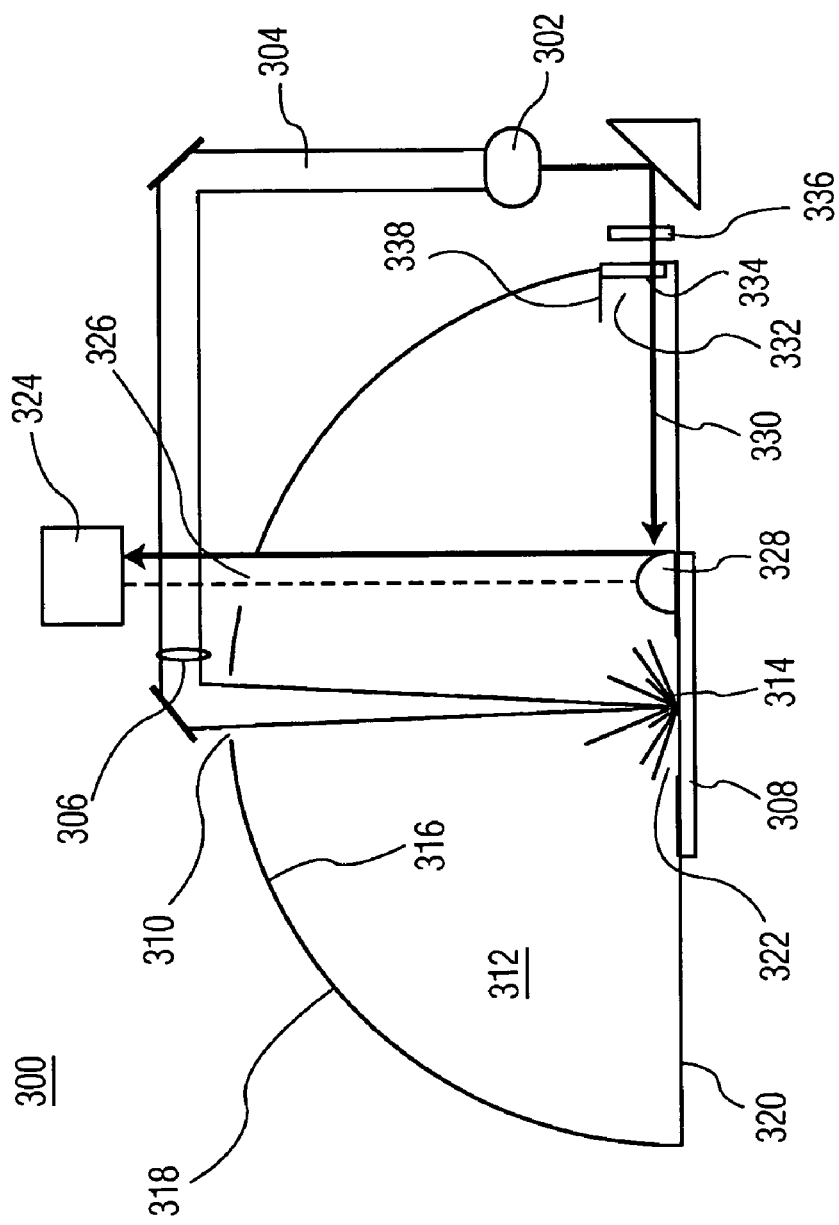
FIG. 3 illustrates an embodiment of a dual beam parousiameter, in accordance with the present disclosure.

Referring to FIG. 3, a radiation source 302, e.g., halogen incandescent lamp, forms an illumination beam 304 using a lens 306, if necessary, to limit the field and to image the lamp aperture on a sample surface 308. The illumination beam 304 passes through a first aperture 310, thus entering the enclosed hemispherical volume 312—formed by a hemispherical dome enclosure 318 and a base 320 capping the bottom portion of the hemispherical dome enclosure 318—of the apparatus 300. The first aperture 310 is formed at the apex of the hemispherical dome enclosure 318 and may be configured as a slit running from the apex of the hemispherical dome enclosure 318 along at least a portion of an arc terminating at the base 320. The illumination beam 304 is configured to move along this arc, thus providing the ability to illuminate the sample surface 308 from multiple angles between 0° and 90°.

Illumination beam 304 impacting the sample surface results in light being reflected by the surface. Generally, this reflected light 314 forms a scatter pattern (not shown), having variations in reflection angle and intensity as well as other optical properties, on a projection screen 316. The degree to which the scatter pattern varies is dependent on the specific texture and optical properties of the sample surface. For example, a smooth, highly reflective surface will produce a correspondingly uniform scatter pattern, while a very rough, matte surface would tend to produce high variability across the entire scatter pattern.

The projection screen 316 is formed on an internal surface of the hemispherical dome enclosure 318. However, the entire internal surface of the hemispherical dome enclosure 318 need not be configured as a projection screen.

The base 320 provides a central opening 322 aligned vertically with the first aperture 310. This opening 322 allows optical access to at least a portion of the sample surface 308 placed against the outside surface of the base 320.

Alternatively, the opening may be replaced by a platform or other supporting means (not shown), wherein the sample surface 308 can be placed during optical properties measurements. However, the base 320 would need to be configured to be removable from the hemispherical dome enclosure 318 and the apparatus 300 would need to be dimensioned to accommodate the sample surface 308 internally.

External to the hemispherical dome enclosure 318, a optical imaging device 324 is positioned. The optical imaging device 324 is vertically aligned with a second aperture 326 formed on the hemispherical dome enclosure 318 and offset from the first aperture 310. Additionally, the optical imaging device 324 and second aperture 326 are vertically aligned with a convex mirror 328 positioned on the base 320, in a manner, which provides a wide-angle image of the projection screen 316 to the optical imaging device 324.

The radiation source also generates a calibration beam 330 simultaneously with the illumination beam 304. The calibration beam is directed through a third aperture 332 positioned on a lower portion of the hemispherical dome enclosure 318 and horizontally aligned with the convex mirror 328. The calibration beam 330 impacts the convex mirror 328 and is reflected to the optical imaging device 324. Alternatively, a second mirror (not shown) may be placed in proximity with the convex mirror and used instead of the convex mirror to reflect the calibration beam to the optical imaging device 324. Various optical components may be placed in the optical path of the calibration beam 330, such as filters 336 and diffusers 334, in order to configure the optical properties of the calibration beam as necessary. A baffle 338 placed above the third aperture 332 prevents the reflected light 314 as well as other ambient light from interfering with the calibration beam 330 and its optical components 334 and 336.

The optical imaging device records both the projection screen image and the calibration beam data simultaneously, where a portion of the recording contains the calibration beam data while the remaining portion of the recording contains the projection screen image. In this way, each recording contains the optical properties of the sample surface 308 as projected on the projection screen 316 as well as calibration data. The calibration data is used to characterize optical properties of the illumination beam 304, thus allowing optical variations in the output from the radiation source 302 to be compensated for during analysis of the projection screen image.

Figure 4:
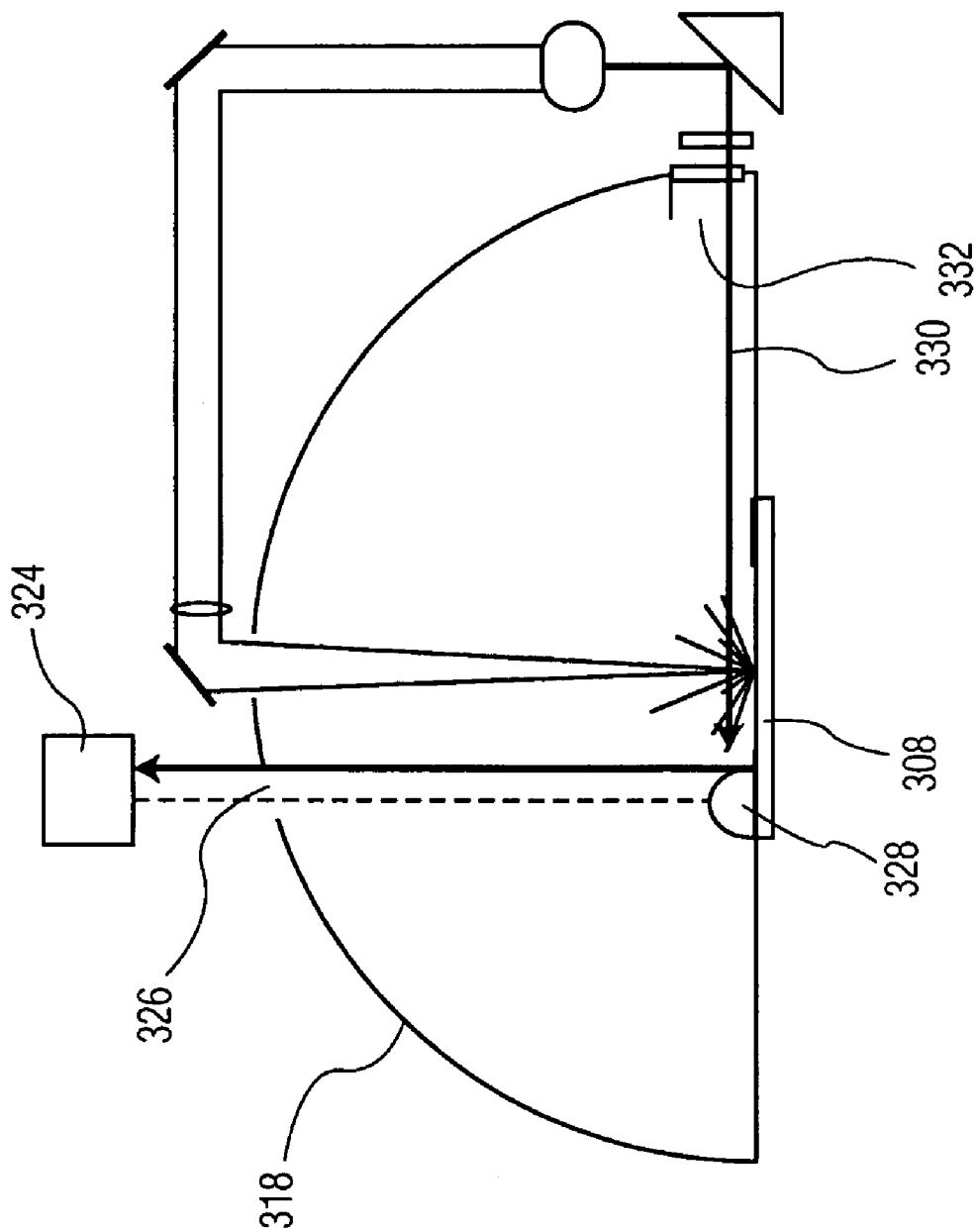
FIG. 4 illustrates another embodiment of a dual beam parousiameter, in accordance with the present disclosure.

The apparatus 300 may be susceptible to producing stray light in the optical imaging device light path, since the optical imaging device 324 must look through the illumination beam 304 when the illumination beam 304 is positioned at the apex of the first aperture 310. Therefore, in another embodiment as shown in FIG. 4, the convex mirror 328 is placed at the far end of the hemispherical dome enclosure 318 in relation to the calibration beam 330. Additionally, the optical imaging device 324 and the second aperture 326 are positioned in vertical alignment with the convex mirror 328. The calibration beam 330 travels across the sample surface 308 to the convex mirror 328 and is reflected up to the optical imaging device 224.

Figure 5:
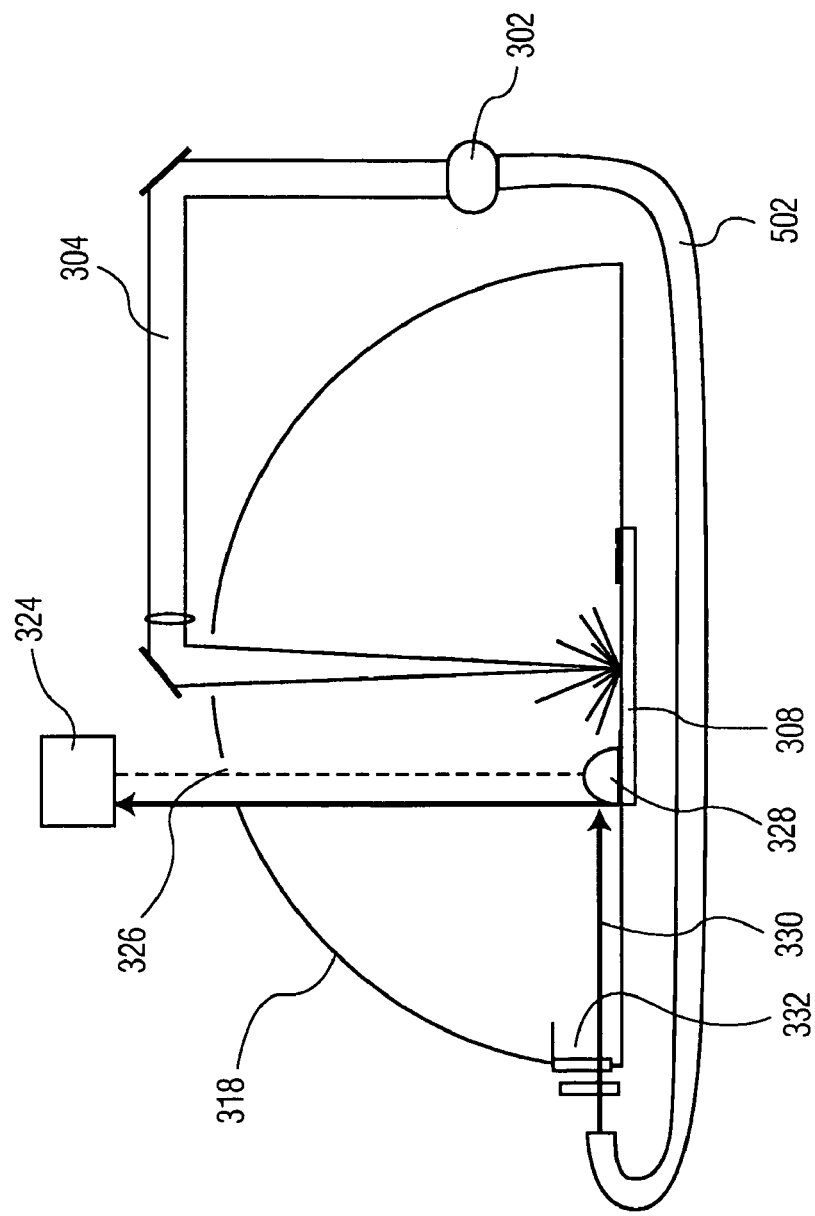
FIG. 5 illustrates another embodiment of a dual beam parousiameter, in accordance with the present disclosure.

Yet another embodiment is shown in FIG. 5, which combines aspects of both FIG. 3 and FIG. 4. As in FIG. 4, the convex mirror 328, the second aperture 326, and the optical imaging device are placed outside the path of the illumination beam 304. The third aperture is formed on a portion of the hemispherical dome enclosure 318 closest to the convex mirror 328. A fiber-optic filament 502 directs the calibration beam 330 from the radiation source 302 to the third aperture 332.

Figure 6:
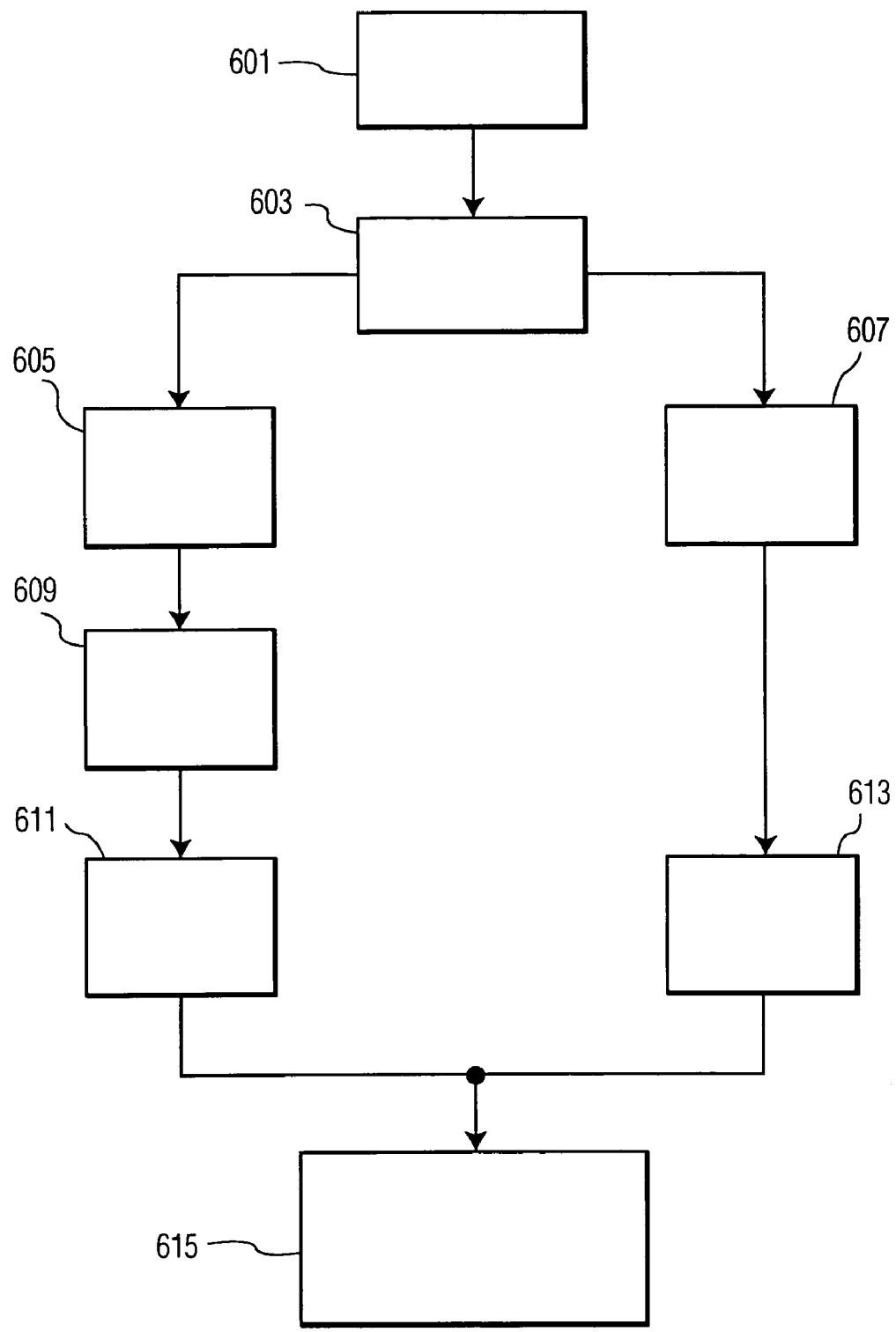
FIG. 6 is a flowchart illustrating the steps for measuring optical parameters of a sample surface using a dual beam parousiameter, in accordance with the present disclosure.

Referring to the flowchart of FIG. 6, the steps required for measuring optical parameters of a sample surface are shown. Beginning with step 601, a sample surface 308 is positioned under the base 320 so that a portion of the sample surface 308 is aligned with the opening 322. In step 603 a radiation source 302 is activated, producing an illumination beam 304, which illuminates the sample surface 308 in step 605. Additionally, a calibration beam 330 is simultaneously transmitted from the radiation source 302 in step 607. Light scattered by the sample surface 308 is projected on to a projection screen 316 in step 609. Proceeding to step 611, an optical imaging device 324 images the projection screen, while simultaneously receiving the calibration beam in step 613. The process concludes with step 615, where an electronic image is created having screen data in one portion of the electronic image and calibration data in a second portion of the electronic image.

The light source 302 used in the present disclosure is not limited to a halogen bulb but may include discharge lamps, e.g., metal halide, mercury vapor, sodium vapor, etc., and laser sources. Discharge lamps generally provide higher intensity light output then does halogen.

Discharge lamps have a much greater tendency towards non-uniform light intensity and color distribution between various emission directions over time. For example, a discharge lamp may radiate a yellowish-white light in a set of directions perpendicular to the lamp's long axis, while a more bluish-white light is emitted along the long axis. The same applies for intensity.

Additionally, as a discharge lamp heats up, the shape and location of the discharge, i.e., the actual point within the lamp that produces the illumination, changes thus further altering the lamp characteristics in a non-uniform manner.

Figure 7:
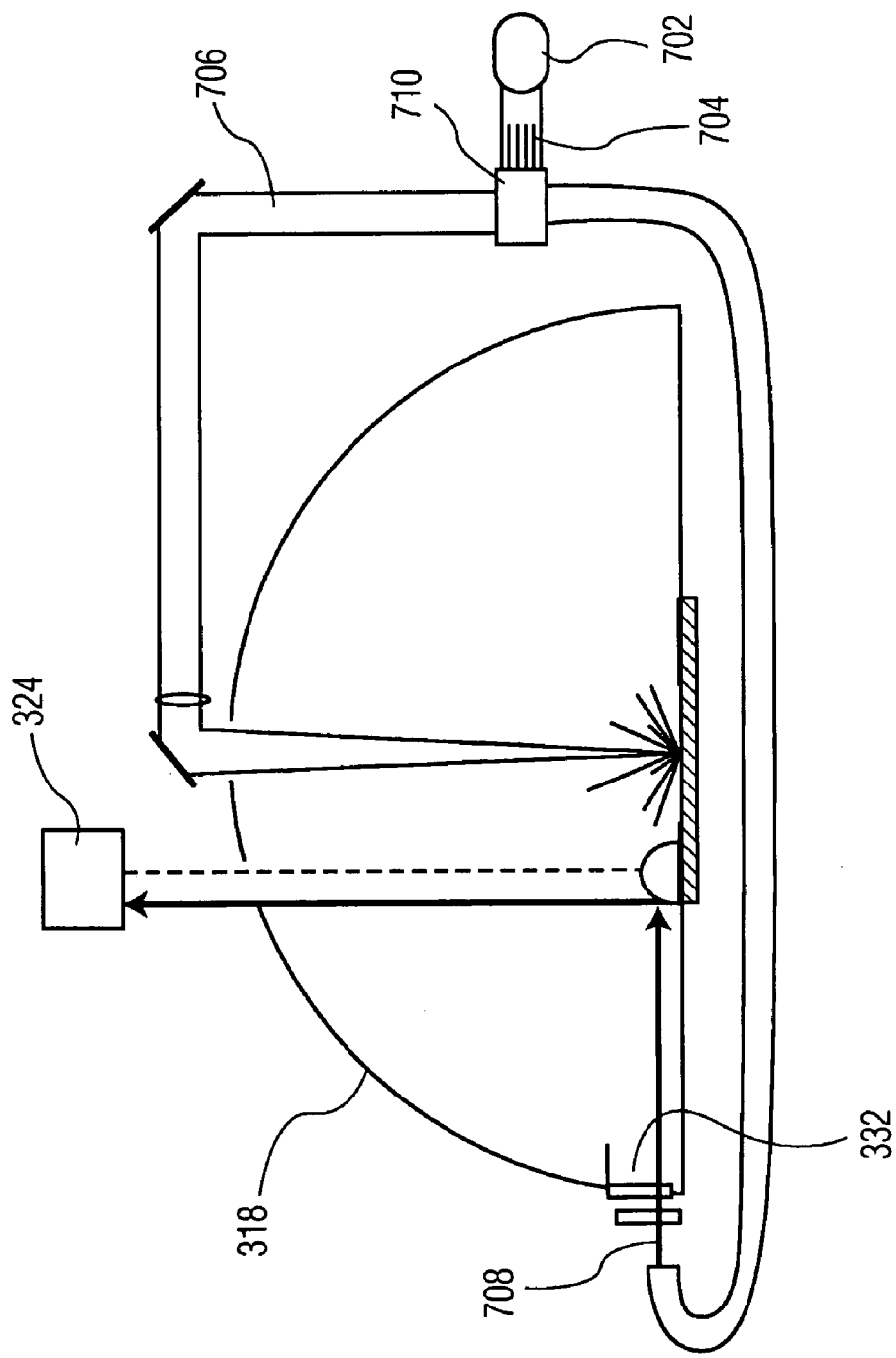
FIG. 7 illustrates yet another embodiment of a dual beam parousiameter, in accordance with the present disclosure.

The above-described embodiments would not be entirely effective when using a discharge lamp. Accordingly, another embodiment is provided in FIG. 7, which overcomes these non-uniformities characteristic of discharge lamps. Referring now to the embodiment of FIG. 7, the parousiameter 700 is constructed in much the same way as shown in FIG. 5.

However, the light source 702 in the present embodiment is a discharge lamp, which outputs an initial beam of light 704. The initial beam 704 is then split into a illumination beam 706 and a calibration beam 708 using an amplitude beam splitter 710, such as a metalized pellicle or a cube splitter. As in the previous embodiments, the illumination beam is directed to the apex of the hemispherical dome enclosure 318, while the calibration beam is directed through the third aperture 332 and onward towards the optical imaging device 324. Since both the illumination beam 706 and the calibration beam 708 originate from the same initial beam 704, both share many of the same characteristics and thus can be used to compensate for a wider range of factors It should be noted that the present embodiment works equally well with an incandescent bulb or even a laser source. In fact when using a laser source, variations in polarization distribution can also be compensated for.

Images can be obtained with video frequency, e.g. 25 Hz using a video-imaging device is employed. There is a provision for continuous adjustment of the illumination beam ascension and sample azimuth, so that a complete set of, say, a few hundred images can be obtained in a few minutes to form the basis of further data processing.

Additionally, if a color video-imaging device is used, the same measurement also provides data about the wavelength dependent behavior of the sample. Color video uses three wavelength bands, which is not a real color measurement in the CIE sense, but it brings very useful direction-dependent color information of the sample. This is of special interest for diffractive surfaces such as holograms.

Normally, the imaging device is aimed to view the image on the screen, while the sample itself is not visible for the imaging device. In a special embodiment of the apparatus there are provisions to allow the sample itself to be imaged directly by the imaging device. The imaging device may be aimed at the sample by slightly turning the imaging device from the mirror to the sample. In this viewing mode the sample may be illuminated by diffuse light obtained through one or more additional lamps that illuminate the inside of the dome. The sample may also be illuminated by a collimated beam of light or by a bright spot projected on the screen. The specular reflection of the beam or spot off the sample may fall in the imaging device or to the side of the imaging device, depending on the desired characteristic of the sample to be observed. The viewing mode allows different characteristics of the sample texture to be retrieved, because the sample is viewed directly and not via a Fourier-like transformation.

The screen may be used in reflection or transmission and has the usual properties of a projection screen. The two-dimensional image formed on the screen represents the angular distribution of the radiation scattered by a sample arranged at the sample location. The image is therefore a Fourier-like transform of the physical properties of the sample, in which a spatial variation in physical properties of the sample is transformed to an angular variation of radiation energy. The use of an imaging device, e.g. a video camera, allows a fast capture of the image, being the full distribution of the scattered radiation.

The sample surface may be investigated in reflection or in transmission. In the latter case the illumination beam and the scattered radiation to be detected are at opposite sides of the sample, and the measurement is indicative not only for the physical properties of the entrance and/or exit surface of the sample but also of its interior. The sample may be mounted on an adjustable stage, to allow changes in the azimuth of the sample.

The described embodiments of the present invention are intended to be illustrative rather than restrictive, and are not intended to represent every embodiment of the present invention. Various modifications and variations can be made without departing from the spirit or scope of the invention as set forth in the following claims both literally and in equivalents recognized in law.

The invention claimed is:

1. An apparatus for characterizing optical appearance of a sample surface, said apparatus comprising:
   an upper housing having a first aperture at a central position on a top surface, a second aperture formed at a position offset from said first aperture, and a third aperture formed at a bottom position of said upper housing and perpendicular to said first aperture, said upper housing having an inside surface configured as a projection screen;
   a base configured and positioned to support said upper housing, said base and upper housing forming an enclosed volume, and said base having an opening being positioned opposite said first aperture, so that when said sample surface is positioned against an outside surface of said base at least a portion of said sample surface is visible through said first aperture and said opening;
   a secondary mirror disposed on an inside surface of said base and optically communicating with said second aperture $_{326}$ and said third aperture; a radiation source positioned outside said enclosed volume;
   a first radiation beam produced by said radiation source, said first radiation beam being directed along a first optical path originating at said radiation source, passing through said first aperture, said opening and terminating at said sample surface at an incident angle;
   an optical imaging device, positioned outside said enclosed volume and in optical communication with said second aperture and said secondary mirror; and
   a second radiation beam emitted by said radiation source simultaneous to emission of said first radiation beam, said second radiation beam being directed along a second optical path originating at said radiation source, entering said enclosed volume through said third aperture, redirecting through said second aperture, and terminating at said optical imaging device.

2. The apparatus of claim 1, wherein said first radiation beam and said second radiation beam originate from an initial radiation beam produced by said radiation source, said initial radiation beam being directed towards a beam splitting means for separating said initial radiation beam into said first radiation beam and said second radiation beam.

3. The apparatus of claim 1, wherein one or more of a portion of said first optical path and said second optical path is through a fiber-optic filament.

4. The apparatus of claim 1, wherein said upper housing is dimensioned as a hemispherical dome and said enclosed volume is an enclosed hemispherical volume.

5. The apparatus of claim 4, wherein said first aperture is dimensioned as a slit along at least a portion of an arc from said apex to said base; and said first optical path is movable along said first aperture such that said incident angle is selectable in the range between 0° and 90°.

6. The apparatus of claim 1, wherein said radiation source generates radiation beams of visible light.

7. The apparatus of claim 1, further comprising a moveable stage for positioning said sample surface.

8. The apparatus of claim 1, wherein said first radiation beam is positionable for illuminating through said sample surface when said sample surface is optically transmissive such that at least a portion of said illumination is transmitted through said sample surface and into said hemispheric volume.

9. The apparatus of claim 1, further comprising a third radiation beam generated by said radiation source and directed towards illuminating said sample surface from a side not in optical communication with said first radiation beam, said third radiation beam being employed when characterization of optical appearance is performed in a transmission mode.

10. The apparatus of claim 1, further comprising a baffle positioned on said inside surface of said upper housing along at least a portion of said third aperture, said baffle 338 being configured to block scattered radiation from interfering with any optical components forming said second optical path.

11. The apparatus of claim 1, wherein said secondary mirror is a convex mirror positioned to reflected at least a portion of said projection screen to said optical imaging device.

* * * * *